United States Patent [19]
Li et al.

[11] Patent Number: 6,110,720
[45] Date of Patent: Aug. 29, 2000

[54] ORPINOMYCES CELLULASE CELE PROTEIN AND CODING SEQUENCES

[75] Inventors: Xin-Liang Li; Lars G. Ljungdahl; Huizhong Chen, all of Athens, Ga.

[73] Assignee: University of Georgia Research Foundation, Inc., Athens, Ga.

[21] Appl. No.: 09/118,324

[22] Filed: Jul. 17, 1998

[51] Int. Cl.[7] .............................. C12N 9/42; C12N 15/56
[52] U.S. Cl. ................. 435/209; 435/252.3; 435/252.33; 536/23.2
[58] Field of Search ............................ 435/252.3, 252.33, 435/209; 536/23.2

[56] References Cited

FOREIGN PATENT DOCUMENTS

WO 98/14597  9/1998  WIPO .

OTHER PUBLICATIONS

Béguin, P. (1983) "Detection of Cellulase Activity in Polyacrylamide Gels Using Congo Red–Stained Agar Replicas" *Analytical Biochem.* 131:333–336.

Black et al. (1994) "Xylanase B from *Neocallimastix patriciarum* contains a non–catalytic 455–residue linker sequence comprised of 57 repeats of an octapeptide" *Biochem. J.* 299:381–387.

Borneman et al. (1989) "Fermentation Products and Plant Cell Wall–Degrading Enzymes Produced by Monocentric and Polycentric Anaerobic Ruminal Fungi" *Applied and Environ. Microbiol.* 55:1066–1073.

Chen et al. (1998) "Two genes of the anaerobic fungus *Orpinomyces sp.* strain PC–2 encoding cellulases with endoglucanase activities may have arisen by gene duplication" *FEMS Microbiol. Letts.* 159:63–68.

Chen et al. (1997) "Sequencing of a 1,3–1,4–β–D–Glucanase (Lichenase) from the Anaerobic Fungus Orpinomyces Strain PC–2: Properties of the Enzyme Expressed in *Escherichia coli* and Evidence that the Gene Has a Bacterial Origin" *J. Bacteriol.* 179:6028–6034.

Choi, S.–K. And Ljungdahl, L.G. (1996) "Structural Role of Calcium for the Organization of the *Cellulosome* of *Clostridium thermocellum*" *Biochemistry* 35:4906–4910.

Dalrymple et al. (1997) "Three *Neocallimastix patriciarum* esterases associated with the degradation of complex polysaccharides are members of a new family of hydrolases" *Microbiology* 143:2605–2614.

Denman et al. (1996) "Characterization of a *Neocallimastix patriciarum* Cellulase cDNA (celA) Homologous to *Trichoderma reesei* Cellobiohydrolase II" *Appl. Environ. Microbiol.* 62:1889–1896.

Durand et al. (1996) "Molecular characterization of xyn3, a member of the endoxylanase multigene family of the rumen anaerobic fungus *Neocallimastix frontalis*" *Curr. Genet.* 30:531–540.

Fanutti et al. (1995) "The Conserved Noncatalytic 40–Residue Sequence in Cellulases and Hemicellulases from Anaerobic Fungi Functions as a Protein Docking Domain" *J. Biol. Chem.* 270:29314–29322.

GenBank Accession Number AF015248, submitted on Jul. 20, 1997.

GenBank Accession Number U97153, released in Apr. 1998.

Gilbert et al. (1992) "Homologous catalytic domains in a rumen fungal xylanase: evidence for gene duplication and prokaryotic origin" *Mol. Microbiol.* 6:2065–2072.

Henrissat, B. and Bairoch, A. (1993) "New families in the classification of glycosyl hydrolases based on amino acid sequence similarities" *Biochem. J.* 293:781–788.

Knowles et al. (1987) "Cellulase families and their genes" *Trends Biotechnol.* 5:255–261.

Li et al. (1997) "Monocentric and Polycentric Anaerobic Fungi Produce Structurally Related Cellulases and Xylanases" *Appl. Environ. Microbiol.* 63:628–635.

Li et al. (1997) "Two Cellulases, CelA and CelC, from the Polycentric Anaerobic Fungus Orpinomyces Strain PC–2 Contain N–Terminal Docking Domains for a Cellulase–Hemicellulase Complex" *Appl. Environ. Microbiol.* 63:4721–4728.

Li et al. (1997) "High Molecular Weight Cellulase/Hemicellulase Complexes of Anaerobic Fungi" *Abstr.* 97th *Gen. Meet. Am. Soc. Microbiol.*, American Society for Microbiology, Washington, DC. p. 424.

Li, X.–L. And Ljungdahl, L.G. (1994) "Cloning, Sequencing, and Regulation of a Xylanase Gene from the Fungus *Aureobasidium pulllans* Y–2311–1" *Appl. Environ. Microbiol.* 60:3160–3166.

Liu et al. (1997) "An endoglucanase from the anaerobic fungus *Orpinomyces joyonii*: characterization of the gene and its product" *Can. J. Microbiol.* 43:477–485.

Millward–Sadler et al. (1996) "Evidence that the Piromyces gene family encoding endo–1,4–mannanases arose through gene duplication" *FEMS Microbiol. Letts.* 141:183–188.

Reymond et al. (1991) "Molecular cloning of genes from the rumen anaerobic fungus *Neocallismastix frontalis*: expression during hydrolase induction" *FEMS Microbiol. Letts.* 77:107–112.

Xue et al. (1992) "Cloning and expression of multiple cellulase cDNAs from the anaerobic rumen fungus *Neocallimastix patriciarum* in *Escherichia coli*" *J. Gen. Microbiol.* 138:1413–1420.

Zhou et al. (1994) "Intronless celB from the anaerobic fungus *Neocallimastix patriciarum* encodes a modular family A endoglucanase" *Biochem. J.* 297:359–364.

*Primary Examiner*—Charles L. Patterson, Jr.
*Attorney, Agent, or Firm*—Greenlee, Winner and Sullivan, P.C.

[57] ABSTRACT

A CDNA designated celE cloned from Orpinomyces PC-2 encodes a polypeptide (CelE) of 477 amino acids. CelE is highly homologous to CelB of Orpinomyces (72.3% identity) and Neocallimastix (67.9% identity), and like them, it has a non-catalytic repeated peptide domain (NCRPD) at the C-terminal end. The catalytic domain of CelE is homologous to glycosyl hydrolases of Family 5, found in several anaerobic bacteria. The gene of celE is devoid of introns. The recombinant proteins CelE and CelB of Orpinomyces PC-2 randomly hydrolyze carboxymethylcellulose and cello-oligosaccharides in the pattern of endoglucanases.

9 Claims, 2 Drawing Sheets

```
  1 MKFFKNTLALLTLVIAGSNAMRNIPSKDLVKELNIGWNLGNALDAHCLDK  50
    |||: |.|.||.|||||::|||||.||:|||||.|||.|||.||| |::.
  1 MKFL.NSLSLLGLVIAGCEAMRNISSKELVKELTIGWSLGNTLDASCVET  49

51 LDYNKDQLASETCWANPKATPGLFSALKNQGFNVFRIPTTWTGHFGNGPD 100
    |:|.||| ||||||:|.|.|.:|: |.: |||.|||||||.||||::||
 50 LNYSKDQTASETCWGNVKTTQELYYKLSDLGFNTFRIPTTWSGHFGDAPD  99

101 YKISDVWMRRVHEVVDYALNTGSYVILNIHHENWNYAFSNNLQKAKPILA 150
    |||||||:|||||||||||||:|.||||||.||||| .||:.||.||.
100 YKISDVWMKRVHEVVDYALNTGGYAILNIHHETWNYAFQKNLESAKKILV 149

151 AIWKQIAAEFANYDEHLIFEGMNEPRKVDHPNEWNGGDQEGWDFVNEMNA 200
    ||||||||||::||||||||||||||||:.|.||.||||||||:||||||
150 AIWKQIAAEFGDYDEHLIFEGMNEPRKVGDPAEWTGGDQEGWNFVNEMNA 199

201 VFLQTVRASGGNNAIRHLMIPTYAACVNDGALESYVRKFPTNDNKVIASV 250
    :|:.|:||.|||| |||||||||||:||||.:::.: |:|..|:|||.|:
200 LFVKTIRATGGNNANRHLMIPTYAASVNDGSINNF..KYPNGDDKVIVSL 247

251 HSYVPYNFALNTGAGAEKTFGSTSDIEWAMNNIKRFLVDRNIPVIIGEFG 300
    ||| ||||||.|:|| ..| ...:|:.||.|.. ::.:.|||||||.
248 HSYSPYNFALNNGPGAISNFYDGNEIDWVMNTINSSFISKGIPVIIGEFV 297

301 AMNRDNESERARWAEYYIKSATAMGVPCVLWDNGYTQGTGELFGVIDRNS 350
    ||||||.:|.||.|||||.|||:|:|||:|||||:|.|| ||:|||.|
298 AMNRDNEDDRERWQEYYIKKATALGIPCVIWDNGYFEGEGERFGIIDRKS 347

351 YRIIFQQFINGLMKGLGGKKTVAPAPTTTITTTTTVKVQPTNNNECFSTR 400
    ..:||..:|||||||||:.|    |.|. |||||.|||| ||||||||
348 LNVIFPKLINGLMKGLGDEK...PKTTIRRTTTTTVQVQPTINNECFSTR 394

401 LGYSCCNGCDVFYTDNDGKWGVENGNWCGIKSSCDNNQRYCWSERLGYPC 450
    |||||||| ||:|||||||.||||||||||||||||:||| |||||||||
395 LGYSCCNGFDVLYTDNDGQWGVENGNWCGIKSSCGNNQRQCWSERLGYPC 444

451 CQYTTNVEYTDNDGRWGVENGNWCGIY 477
    ||||||.||||||||||||||||||||
445 CQYTTNAEYTDNDGRWGVENGNWCGIY 471
```

FIG. 1

SEQUENCE LISTING

<160> NUMBER OF SEQ ID NOS: 5

<210> SEQ ID NO 1
<211> LENGTH: 1532
<212> TYPE: DNA
<213> ORGANISM: Orpinomyces sp. PC-2
<220> FEATURE:
<221> NAME/KEY: CDS
<222> LOCATION: (39)..(1472)

<400> SEQUENCE: 1

```
aaaataataa ataacttatt tattaaatat cagtaaaa atg aag ttt ttc aaa aac      56
                                           Met Lys Phe Phe Lys Asn
                                             1               5 act tta gct tta ctc acc tta gtc att gct ggt tca aat gct atg aga     104
Thr Leu Ala Leu Leu Thr Leu Val Ile Ala Gly Ser Asn Ala Met Arg
             10                  15                  20 aat att cca tcc aaa gat tta gtt aag gaa tta aac att ggt tgg aat     152
Asn Ile Pro Ser Lys Asp Leu Val Lys Glu Leu Asn Ile Gly Trp Asn
         25                  30                  35 tta ggt aat gct tta gat gct cat tgt tta gat aaa tta gat tat aat     200
Leu Gly Asn Ala Leu Asp Ala His Cys Leu Asp Lys Leu Asp Tyr Asn
     40                  45                  50 aaa gat caa ctt gct tct gaa act tgt tgg gct aat cca aag gct act     248
Lys Asp Gln Leu Ala Ser Glu Thr Cys Trp Ala Asn Pro Lys Ala Thr
 55                  60                  65                  70 cca gga ctt ttc agt gca tta aag aat caa ggt ttt aat gtt ttc cgt     296
Pro Gly Leu Phe Ser Ala Leu Lys Asn Gln Gly Phe Asn Val Phe Arg
             75                  80                  85
```

-continued

```
att cca acc act tgg acc ggt cac ttt ggt aat ggt cca gat tac aaa    344
Ile Pro Thr Thr Trp Thr Gly His Phe Gly Asn Gly Pro Asp Tyr Lys
             90                  95                 100 att agt gat gtt tgg atg aga aga gtt cat gaa gtt gtt gat tat gct    392
Ile Ser Asp Val Trp Met Arg Arg Val His Glu Val Val Asp Tyr Ala
        105                 110                 115 ctt aac act gga agc tac gtc atc tta aat att cac cat gaa aat tgg    440
Leu Asn Thr Gly Ser Tyr Val Ile Leu Asn Ile His His Glu Asn Trp
    120                 125                 130 aat tat gct ttc tct aac aat tta caa aag gca aaa cca att tta gct    488
Asn Tyr Ala Phe Ser Asn Asn Leu Gln Lys Ala Lys Pro Ile Leu Ala
135                 140                 145                 150 gct atc tgg aaa caa att gct gct gaa ttc gct aac tat gat gaa cat    536
Ala Ile Trp Lys Gln Ile Ala Ala Glu Phe Ala Asn Tyr Asp Glu His
                155                 160                 165 tta att ttc gaa ggt atg aat gaa cca aga aag gtt gat cat cca aat    584
Leu Ile Phe Glu Gly Met Asn Glu Pro Arg Lys Val Asp His Pro Asn
            170                 175                 180 gaa tgg aat ggt ggt gac caa gaa ggt tgg gac ttc gtt aat gaa atg    632
Glu Trp Asn Gly Gly Asp Gln Glu Gly Trp Asp Phe Val Asn Glu Met
        185                 190                 195 aat gct gtc ttc ctt caa act gtt cgt gcc tct ggt ggt aac aat gct    680
Asn Ala Val Phe Leu Gln Thr Val Arg Ala Ser Gly Gly Asn Asn Ala
    200                 205                 210 att cgt cac ctt atg att cca act tat gct gct tgt gtt aac gat ggt    728
Ile Arg His Leu Met Ile Pro Thr Tyr Ala Ala Cys Val Asn Asp Gly
215                 220                 225                 230 gct ctt gaa tct tac gtt aga aaa ttc cca act aat gat aat aag gtt    776
Ala Leu Glu Ser Tyr Val Arg Lys Phe Pro Thr Asn Asp Asn Lys Val
                235                 240                 245 att gct tct gtc cac tct tat gtt cca tat aac ttt gcc tta aat act    824
Ile Ala Ser Val His Ser Tyr Val Pro Tyr Asn Phe Ala Leu Asn Thr
            250                 255                 260 ggc gcc ggt gct gaa aag act ttc ggt tcc act agc gat att gaa tgg    872
Gly Ala Gly Ala Glu Lys Thr Phe Gly Ser Thr Ser Asp Ile Glu Trp
        265                 270                 275 gct atg aac aac atc aag aga ttc tta gtt gac aga aat att cca gtt    920
Ala Met Asn Asn Ile Lys Arg Phe Leu Val Asp Arg Asn Ile Pro Val
    280                 285                 290 ata att ggt gaa ttc gga gct atg aac cgt gac aat gaa tct gaa cgt    968
Ile Ile Gly Glu Phe Gly Ala Met Asn Arg Asp Asn Glu Ser Glu Arg
295                 300                 305                 310 gct aga tgg gct gaa tac tac att aag agt gcc act gct atg ggt gtt   1016
Ala Arg Trp Ala Glu Tyr Tyr Ile Lys Ser Ala Thr Ala Met Gly Val
                315                 320                 325 cca tgt gtc tta tgg gat aat ggt tac act caa ggt act ggt gaa ctt   1064
Pro Cys Val Leu Trp Asp Asn Gly Tyr Thr Gln Gly Thr Gly Glu Leu
            330                 335                 340 ttc ggt gtt att gac cgt aac tct tac aga atc att ttc caa caa ttc   1112
Phe Gly Val Ile Asp Arg Asn Ser Tyr Arg Ile Ile Phe Gln Gln Phe
        345                 350                 355 att aat ggc tta atg aag gga tta ggt ggt aag aag acc gtt gct cca   1160
Ile Asn Gly Leu Met Lys Gly Leu Gly Gly Lys Lys Thr Val Ala Pro
    360                 365                 370 gct cca act act act att act act act act gtt aaa gtt caa cca       1208
Ala Pro Thr Thr Thr Ile Thr Thr Thr Thr Val Lys Val Gln Pro
375                 380                 385                 390 act aat aat aat gaa tgt ttc agt act aga ctt ggt tac agc tgt tgt   1256
Thr Asn Asn Asn Glu Cys Phe Ser Thr Arg Leu Gly Tyr Ser Cys Cys
```

-continued

```
                     395                 400                 405
aat ggt tgt gat gtc ttt tac act gat aat gat ggt aaa tgg ggt gtt        1304
Asn Gly Cys Asp Val Phe Tyr Thr Asp Asn Asp Gly Lys Trp Gly Val
            410                 415                 420 gaa aac ggt aac tgg tgt ggt att aag tca tct tgt gat aac aac caa        1352
Glu Asn Gly Asn Trp Cys Gly Ile Lys Ser Ser Cys Asp Asn Asn Gln
                425                 430                 435 cgt tat tgc tgg tct gaa aga ctt ggt tac cca tgt tgt caa tat acc        1400
Arg Tyr Cys Trp Ser Glu Arg Leu Gly Tyr Pro Cys Cys Gln Tyr Thr
    440                 445                 450 acc aat gtt gaa tac acc gat aat gat ggt aga tgg ggt gtt gaa aat        1448
Thr Asn Val Glu Tyr Thr Asp Asn Asp Gly Arg Trp Gly Val Glu Asn
455                 460                 465                 470 ggt aac tgg tgt ggt att tat taa attactaaat aaatttatat aaatagaaat       1502
Gly Asn Trp Cys Gly Ile Tyr
                475 aaattattta gtaaaataaa taaaaaaaaa                                       1532
```

<210> SEQ ID NO 2
<211> LENGTH: 477
<212> TYPE: PRT
<213> ORGANISM: Orpinomyces sp. PC-2

<400> SEQUENCE: 2

```
Met Lys Phe Phe Lys Asn Thr Leu Ala Leu Leu Thr Leu Val Ile Ala
 1               5                  10                  15

Gly Ser Asn Ala Met Arg Asn Ile Pro Ser Lys Asp Leu Val Lys Glu
                20                  25                  30

Leu Asn Ile Gly Trp Asn Leu Gly Asn Ala Leu Asp Ala His Cys Leu
            35                  40                  45

Asp Lys Leu Asp Tyr Asn Lys Asp Gln Leu Ala Ser Glu Thr Cys Trp
    50                  55                  60

Ala Asn Pro Lys Ala Thr Pro Gly Leu Phe Ser Ala Leu Lys Asn Gln
65                  70                  75                  80

Gly Phe Asn Val Phe Arg Ile Pro Thr Thr Trp Thr Gly His Phe Gly
                85                  90                  95

Asn Gly Pro Asp Tyr Lys Ile Ser Asp Val Trp Met Arg Arg Val His
                100                 105                 110

Glu Val Val Asp Tyr Ala Leu Asn Thr Gly Ser Tyr Val Ile Leu Asn
            115                 120                 125

Ile His His Glu Asn Trp Asn Tyr Ala Phe Ser Asn Asn Leu Gln Lys
    130                 135                 140

Ala Lys Pro Ile Leu Ala Ala Ile Trp Lys Gln Ile Ala Ala Glu Phe
145                 150                 155                 160

Ala Asn Tyr Asp Glu His Leu Ile Phe Glu Gly Met Asn Glu Pro Arg
                165                 170                 175

Lys Val Asp His Pro Asn Glu Trp Asn Gly Gly Asp Gln Glu Gly Trp
                180                 185                 190

Asp Phe Val Asn Glu Met Asn Ala Val Phe Leu Gln Thr Val Arg Ala
            195                 200                 205

Ser Gly Gly Asn Asn Ala Ile Arg His Leu Met Ile Pro Thr Tyr Ala
    210                 215                 220

Ala Cys Val Asn Asp Gly Ala Leu Glu Ser Tyr Val Arg Lys Phe Pro
225                 230                 235                 240

Thr Asn Asp Asn Lys Val Ile Ala Ser Val His Ser Tyr Val Pro Tyr
                245                 250                 255
```

```
Asn Phe Ala Leu Asn Thr Gly Ala Gly Ala Glu Lys Thr Phe Gly Ser
            260                 265                 270

Thr Ser Asp Ile Glu Trp Ala Met Asn Asn Ile Lys Arg Phe Leu Val
        275                 280                 285

Asp Arg Asn Ile Pro Val Ile Ile Gly Glu Phe Gly Ala Met Asn Arg
    290                 295                 300

Asp Asn Glu Ser Glu Arg Ala Arg Trp Ala Glu Tyr Tyr Ile Lys Ser
305                 310                 315                 320

Ala Thr Ala Met Gly Val Pro Cys Val Leu Trp Asp Asn Gly Tyr Thr
                325                 330                 335

Gln Gly Thr Gly Glu Leu Phe Gly Val Ile Asp Arg Asn Ser Tyr Arg
            340                 345                 350

Ile Ile Phe Gln Gln Phe Ile Asn Gly Leu Met Lys Gly Leu Gly Gly
        355                 360                 365

Lys Lys Thr Val Ala Pro Ala Pro Thr Thr Thr Ile Thr Thr Thr Thr
    370                 375                 380

Thr Val Lys Val Gln Pro Thr Asn Asn Asn Glu Cys Phe Ser Thr Arg
385                 390                 395                 400

Leu Gly Tyr Ser Cys Cys Asn Gly Cys Asp Val Phe Tyr Thr Asp Asn
                405                 410                 415

Asp Gly Lys Trp Gly Val Glu Asn Gly Asn Trp Cys Gly Ile Lys Ser
            420                 425                 430

Ser Cys Asp Asn Asn Gln Arg Tyr Cys Trp Ser Glu Arg Leu Gly Tyr
        435                 440                 445

Pro Cys Cys Gln Tyr Thr Thr Asn Val Glu Tyr Thr Asp Asn Asp Gly
    450                 455                 460

Arg Trp Gly Val Glu Asn Gly Asn Trp Cys Gly Ile Tyr
465                 470                 475

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
ttatttatgg tggtcaatgg t                                          21

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
atgaagtttt tcaaaaacac tttagc                                     26

<210> SEQ ID NO 5
<211> LENGTH: 471
<212> TYPE: PRT
<213> ORGANISM: Orpinomyces sp. PC-2

<400> SEQUENCE: 5

Met Lys Phe Leu Asn Ser Leu Ser Leu Leu Gly Leu Val Ile Ala Gly
  1               5                  10                  15
```

-continued

```
Cys Glu Ala Met Arg Asn Ile Ser Ser Lys Glu Leu Val Lys Glu Leu
             20                  25                  30

Thr Ile Gly Trp Ser Leu Gly Asn Thr Leu Asp Ala Ser Cys Val Glu
         35                  40                  45

Thr Leu Asn Tyr Ser Lys Asp Gln Thr Ala Ser Glu Thr Cys Trp Gly
     50                  55                  60

Asn Val Lys Thr Thr Gln Glu Leu Tyr Tyr Lys Leu Ser Asp Leu Gly
 65                  70                  75                  80

Phe Asn Thr Phe Arg Ile Pro Thr Thr Trp Ser Gly His Phe Gly Asp
                 85                  90                  95

Ala Pro Asp Tyr Lys Ile Ser Asp Val Trp Met Lys Arg Val His Glu
                100                 105                 110

Val Val Asp Tyr Ala Leu Asn Thr Gly Gly Tyr Ala Ile Leu Asn Ile
            115                 120                 125

His His Glu Thr Trp Asn Tyr Ala Phe Gln Lys Asn Leu Glu Ser Ala
        130                 135                 140

Lys Lys Ile Leu Val Ala Ile Trp Lys Gln Ile Ala Ala Glu Phe Gly
145                 150                 155                 160

Asp Tyr Asp Glu His Leu Ile Phe Glu Gly Met Asn Glu Pro Arg Lys
                165                 170                 175

Val Gly Asp Pro Ala Glu Trp Thr Gly Gly Asp Gln Glu Gly Trp Asn
                180                 185                 190

Phe Val Asn Glu Met Asn Ala Leu Phe Val Lys Thr Ile Arg Ala Thr
            195                 200                 205

Gly Gly Asn Asn Ala Asn Arg His Leu Met Ile Pro Thr Tyr Ala Ala
        210                 215                 220

Ser Val Asn Asp Gly Ser Ile Asn Asn Phe Lys Tyr Pro Asn Gly Asp
225                 230                 235                 240

Asp Lys Val Ile Val Ser Leu His Ser Tyr Ser Pro Tyr Asn Phe Ala
                245                 250                 255

Leu Asn Asn Gly Pro Gly Ala Ile Ser Asn Phe Tyr Asp Gly Asn Glu
                260                 265                 270

Ile Asp Trp Val Met Asn Thr Ile Asn Ser Ser Phe Ile Ser Lys Gly
            275                 280                 285

Ile Pro Val Ile Ile Gly Glu Phe Val Ala Met Asn Arg Asp Asn Glu
        290                 295                 300

Asp Asp Arg Glu Arg Trp Gln Glu Tyr Tyr Ile Lys Lys Ala Thr Ala
305                 310                 315                 320

Leu Gly Ile Pro Cys Val Ile Trp Asp Asn Gly Tyr Phe Glu Gly Glu
                325                 330                 335

Gly Glu Arg Phe Gly Ile Ile Asp Arg Lys Ser Leu Asn Val Ile Phe
            340                 345                 350

Pro Lys Leu Ile Asn Gly Leu Met Lys Gly Leu Gly Asp Glu Lys Pro
        355                 360                 365

Lys Thr Thr Ile Arg Arg Thr Thr Thr Thr Val Gln Val Gln Pro
        370                 375                 380

Thr Ile Asn Asn Glu Cys Phe Ser Thr Arg Leu Gly Tyr Ser Cys
385                 390                 395                 400

Asn Gly Phe Asp Val Leu Tyr Thr Asp Asn Asp Gly Gln Trp Gly Val
                405                 410                 415

Glu Asn Gly Asn Trp Cys Gly Ile Lys Ser Ser Cys Gly Asn Asn Gln
            420                 425                 430
```

-continued

```
Arg Gln Cys Trp Ser Glu Arg Leu Gly Tyr Pro Cys Cys Gln Tyr Thr
        435                 440                 445

Thr Asn Ala Glu Tyr Thr Asp Asn Asp Gly Arg Trp Gly Val Glu Asn
    450                 455                 460

Gly Asn Trp Cys Gly Ile Tyr
465                 470
```

ORPINOMYCES CELLULASE CELE PROTEIN AND CODING SEQUENCES

ACKNOWLEDGEMENT OF FEDERAL RESEARCH SUPPORT

This invention was made, at least in part, with funding from the United States Department of Energy (Grant No. DE-FG05 93ER 20127). Accordingly, the United States Government has certain rights in this invention.

CROSS REFERENCE TO RELATED APPLICATIONS not applicable

BACKGROUND OF THE INVENTION

The field of the present invention is the area of cellulolytic enzymes, nucleotide sequences encoding them and recombinant host cells and methods for producing them.

Cellulosic biomass, photosynthesized by solar energy with $CO_2$ and $H_2O$, is one of the most important renewable energy resources on earth. Its effective utilization through biological processes is one approach to overcoming the shortage of foods, feeds and fuels, expected as a consequence of the explosive increase in human population [Ohmiya et al. (1997)]. Several types of enzymes are required for complete hydrolysis of cellulose to glucose, including endoglucanase, exoglucanase or cellobiohydrolase and β-glucosidase [Filho 1996)].

Obligately anaerobic fungi are part of the natural microflora of the alimentary tract of many herbivorous animals. Since the first anaerobic fungus, *Neocallimastix frontalis* was isolated in 1975 from the rumen of sheep [Orpin, G. C. (1975) *J. Gen. Microbiol.* 91, 249–262], at least 17 different anaerobic fungi have been isolated from ruminant and nonruminant herbivores. Anaerobic fungi produce highly active hydrolytic enzymes [Borneman et al.(1989) *Appl. Environ. Microbiol.* 55, 1066–1073], they physically associate with the lignocellulosic tissue of plant fragments, and their hyphae penetrate the plant tissue in vivo [Akin et al.(1983) *Appl. Environ. Microbiol.* 46, 738–748; Thedorou et al. (1996) *Proc. Nutr.* Soc. 55, 913–926]. These fungi are involved in degradation of plant biomass and play an important role in the rumen ecosystem. Several genes coding for hydrolytic enzymes have been cloned and sequenced from the monocentric fungi *Neocallimastix patriciarum* [Gilbert et al. (1992) *Mol. Microbiol.* 6, 2065–2072; Zhou et al. (1994) *Biochem. J..* 297, 359–364; Black et al. (1994) *Biochem. J..* 299, 381–387; Denman et al. (1996) *Appl. Environ. Microbiol.* 62, 1889–1896; Dalrymple et al. (1997) *Microbiology* 143, 2605–2614], *N. frontalis* [Reymond et al. (1991) FEMS Microbiol. Letts. 77, 107–112; Durand et al. (1996) *Curr. Genet.* 30, 531–540], and *Piromyces* sp. [Fanutti et al. (1995) *J. Biol. Chem.* 270, 29314–29322] and from the polycentric fungi *Orpinomyces* PC-2 [Li et al. (1997) *Appl. Environ. Microbiol.* 63, 628–635; Chen et al. (1997) *J. Bacteriol.* 179, 6028–6034] and *Orpinomyces-joyonii* [Liu et al. (1997) *Can. J. Microbiol.* 43, 477–485]. It has been suggested that genes encoding three mannanases of a *Piromyces* sp. [Millward-Sadler et al. (1996) FEMS Microbiol. Letts. 141, 183–188] and two cellobiohydrolases (CelA and CeiC) of *Orpinomyces* PC-2 [Li et al. (1997) *Appl. Environ. Microbiol.* 63, 4721–4728; see also WO 98/14597] resulted from gene duplications. CelB is described in WO 98/14597, incorporated by reference herein in its entirety.

There is a need in the art for a high-specific-activity cellulase in pure form which degrades cellulosic materials, and for DNA encoding this cellulase to enable methods of producing the cellulase in pure form.

SUMMARY OF THE INVENTION

This invention provides a novel cellulase (CelE) from *Orpinomyces* sp. PC-2. CelE has endoglucanase activity, producing primarily cellobiose from carboxymethylcellulose, cellotetraose, β-glucan, lichenin and certain other substrates, and some activity with para-nitrophenyl-β-D-cellobioside as substrate. Avicel, para-nitrophenyl-β-D-glucoside, oat spelt xylan and para-nitrophenyl-β-D-xyloside are not hydrolyzed.

This invention provides a cellulase protein termed "CelE" of *Orpinomyces* PC-2, which has an amino acid sequence as given in Table 3, SEQ ID NO:2. This cellulase is useful for degrading cellulosic materials. The CelE protein as from *Orpinomyces* PC-2 has a calculated molecular weight of 53,635 Da; however the CelE polypeptide of this invention includes proteins or polypeptides having the same or equivalent amino acid sequence and different amounts of glycosylation.

The term CelE refers to the protein or polypeptide having the sequence given in SEQ ID NO:2 herein, equivalent sequences as defined below, and such sequences preceded with a methionine residue immediately preceding the listed sequence. "Substantially pure" CelE is substantially free of naturally associated components when separated from the native contaminants which accompany it in its natural state, either when isolated from *Orpinomyces* or when recombinantly produced in host cells such as *Saccharomyces cerevisiae* or *Escherichia coli*.

A chemically synthesized CelE polypeptide protein is considered an "isolated" protein as is the protein isolated from *Orpinomyces* PC-2 or other host cell in which it is recombinantly produced.

CelE as used herein refers to a polypeptide product which exhibits similar biological activities, i.e., has similar specific activity to natural CelE isolated from *Orpinomyces* PC-2 or chemically synthesized in accordance with the sequence provided in SEQ ID NO:2, enzymatic activity as measured in recognized bioassays, and has substantially the same or "equivalent" amino acid sequence as native CelE (SEQ ID NO:2). It will be understood that polypeptides deficient in one or more amino acids in the amino acid sequence reported herein for naturally occurring CelE, or polypeptides in which one or more amino acids in the amino acid sequence of natural CelE are replaced by other amino acids are within the scope of the invention and have "equivalent" sequences to that given in SEQ ID NO:2, provided that they exhibit the functional (enzymatic) activity of CelE. This invention is intended to embrace all the allelic variations of CelE. Moreover, as noted above, derivatives obtained by simple modification of the amino acid sequence of the naturally-occurring product, e.g., by way of site-directed mutagenesis or other standard procedures, are included within the scope of the present invention. Forms of CelE produced by proteolysis of host cells that exhibit similar biological activities to mature, naturally-occurring CelE are also encompassed by the present invention. The present specification provides guidance to the skilled worker for preparing a large number of equivalent sequences which preferably do not alter areas of homology shared with other cellulases.

This invention also provides for genomic DNA and cDNA and non-naturally occurring recombinant DNA molecules encoding an Orpinomyces CelE protein or polypeptide. The gene encoding CelE is termed celE herein. The cDNA sequence of this gene from Orpinomyces is given in Table 3, SEQ ID NO:1, from nucleotide 39 to 1472. The celE gene is useful for recombinantly expressing the CelE mature protein in S. cerevisiae or other host cells.

Of course, it is recognized by those skilled in the art that the DNA sequences may vary due to the degeneracy of the genetic code and codon usage. All DNA sequences which encode the CelE polypeptide are included in this invention, including DNA sequences (as given in SEQ ID NO:1 from 39 to 1472) having an ATG preceding the coding region for the mature protein.

Additionally, it will be recognized by those skilled in the art that allelic variations may occur in the DNA sequences which will not significantly change activity of the amino acid sequences of the peptides which the DNA sequences encode. All such equivalent DNA sequences are included within the scope of this invention and the definition of the CelE mature protein coding region and CelE signal sequence coding region. The skilled artisan will understand that the amino acid sequence of the exemplified CelE polypeptide and signal peptide can be used to identify and isolate additional, nonexemplified nucleotide sequences which will encode functional equivalents to the polypeptides defined by the amino acid sequences given in SEQ ID NO:1, or an amino acid sequence of greater than 90% identity thereto and having equivalent biological activity. DNA sequences having at least about 85% homology to the DNA sequences of SEQ ID NO:1 and encoding polypeptides with the same function are considered equivalent to the sequences of SEQ ID NO:1 and are included in the definition of "DNA encoding the CelE protein" and the celE gene." Following the teachings herein, the skilled worker will be able to make a large number of operative embodiments having equivalent DNA sequences to those listed herein.

The CelE coding sequences, including or excluding that encoding a signal peptide of this invention can be used to express the cellulase of the present invention in fungal host cells as well as in bacteria, including without limitation, Bacillus spp. Any host cell in which the signal sequence is expressed and processed may be used. Preferred host cells are Aureobasidium species, Aspergillus species, Trichoderma species and *Saccharomyces cerevisiae*, as well as other yeasts known to the art for fermentation, including *Pichia pastoris* (Sreekrishna, K. (1993) in Baltz, R. H., et al. (eds.) *Industrial Microorganisms: Basic and Applied Molecular Genetics*, ASM Press, Washington, D.C. 119–126; Glick, B. R. and Pasternak J. J. (1 994) ASM Press (1994) Washington, D.C. Filamentous fungi such as Aspergillus, Trichoderma, Penicillium, etc. are also useful host organisms for expression of the DNA of this invention. (Van den Handel, C. et al. (1991) In: Bennett, J. W. and Lasure, L. L. (eds.), *More Gene Manipulations in Fungi*, Academy Press, Inc., New York, 397–428).

BRIEF DESCRIPTION OF THE DRAWINGS

FIG. 1 shows a comparison of the deduced amino acid sequences of Orpinomyces PC-2 CelE (top) (SEQ ID NO:2) and CelB (bottom)(SEQ ID NO:5). Amino acid residues with an identical match (|) and those with greater or lesser degrees of conservation (: or.) are indicated. The repeated peptides of the NCRPD and linker regions are underlined and double-underlined.

FIG. 2A is a photograph of a Coomassie brilliant blue stained SDS-polyacrylamide gel. FIG. 2B is a photograph of a zymogram gel. Lane S, protein molecular mass standards; lane 1, CelE (50 µg); lane 2, CelB (55 µg).

DETAILED DESCRIPTION OF THE INVENTION

Figures 2A, 2B:
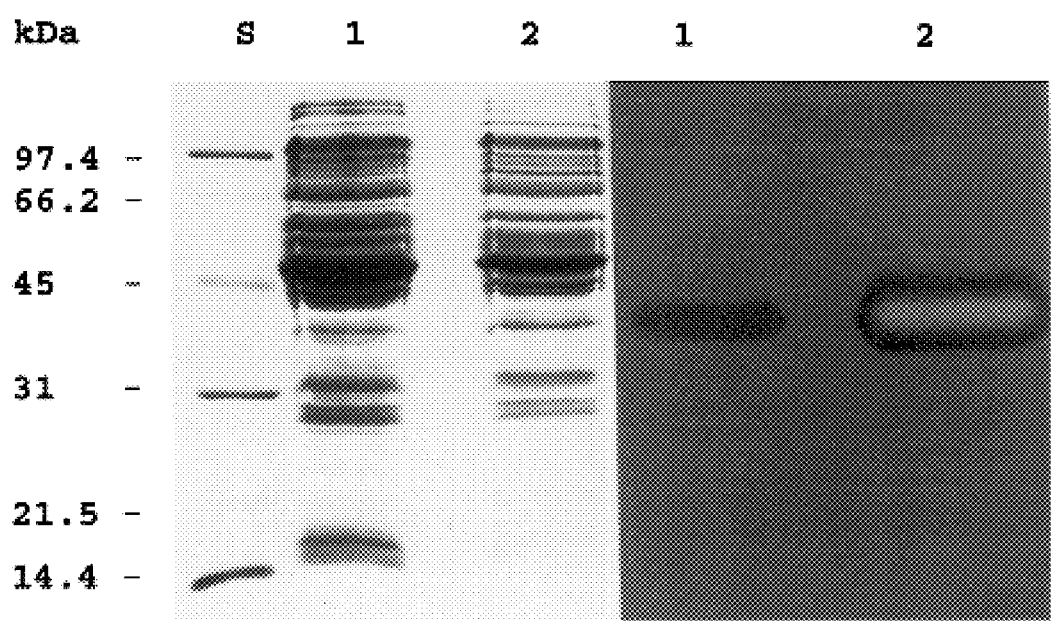
FIGS. 2A–B provide the results of SDS-PAGE and zymogram analysis of the recombinant CelE and CelB.

The amino acids which occur in the various amino acid sequences referred to in the specification have their usual three- and one-letter abbreviations routinely used in the art: A, Ala, Alanine; C, Cys, Cysteine; D, Asp, Aspartic Acid; E, Glu, Glutamic Acid; F, Phe, Phenylalanine; G, Gly, Glycine; H, His, Histidine; I, Ile, Isoleucine; K, Lys, Lysine; L, Leu, Leucine; M, Met, Methionine; N, Asn, Asparagine; P, Pro, Proline; Q, Gln, Glutamine; R, Arg, Arginine; S, Ser, Serine; T, Thr, Threonine; V, Val, Valine; W, Trp, Tryptophan; and Y, Tyr, Tyrosine.

Additional abbreviations used in the present specification include the following: aa, amino acid(s); bp, base pair(s); CD, catalytic domain(s); cDNA, DNA complementary to RNA; GCG, Genetics Computer Group, Madison, Wis; CMC, carboxymethyl cellulose; CMCase, carboxymethyl cellulase; FPase, filter paper-ase; HMWC, high-molecular weight complex(es); IPTG, isopropyl-β-D-thiogalactoside; OSX, oat spelt xylan; ORF, open reading frame; RBB, remazol brilliant blue; RP, repeated peptide(s); pfu, plaque forming units.

Screening of the Orpinomyces PC-2 cDNA library constructed in λZAPII yielded twenty cellulase-producing plaques when 2×10⁵ plaque forming units (PFU) were plated. The positive plaques were further enriched and purified. PCR, restriction enzyme digestion, and sequencing analyses revealed that sixteen out of these plaques represented cDNAs of celA and celB which were isolated in our previous work [Li et al.(1997) *Appl. Environ. Microbiol.* 63, 628–635; Li et al. (1997) *Appl. Environ. Microbiol.* 63, 628–635]. The other four plaques represented four different new cellulase cDNAs (pCEL2, pCEL3, pCEL5 and pCEL8).

Sequencing of the inserts in the plasmids obtained from the plaques by in vivo excision revealed that pCEL3 contained a 1,532 bp (celE) insert (SEQ ID NO:1) with a complete open reading frame (ORF) encoding a polypeptide (CelE) of 477 amino acids with a calculated mass of 53,635 Da (SEQ ID NO:2). Its size is similar to those of CelBs of Orpinomyces PC-2 [Li et al.(1997) *Appl. Environ. Microbiol.* 63, 628–635] and *N. patriciarum* [Durand et al. (1996) *Curr. Genet.* 30, 531–540]. A typical 9 residue poly(A) tail was found at its 3' end. The translation start codon (ATG) for celE was assigned based on the fact that there were stop codons in all three frames preceding the ORF, there was no ATG codon upstream of the proposed ORF, and a typical signal peptide [Von Heijne, G. (1986) *Nucleic Acids Res.* 14, 4683–4690] was located at the N-terminus of the polypeptide. The G+C content of the ORF of celE was 38.6% and that of the 5' and 3' noncoding regions was extremely low (6.4%). High A+T contents have also been found in other cDNAs of the anaerobic fungi [Zhou et al. (1994) *Biochem. J.* 297, 359–364; Li et al.(1997) *Appl. Environ. Microbiol.* 63, 628–635; Chen et al. (1997) *J. Bacteriol.* 179, 6028–6034].

The ORF region of celE genomic DNA was amplified by PCR, and its size was compared with that amplified from cDNA. DNA bands of the same size, 1.4 kb, were visualized using genomic DNA or the cDNA library as templates, indicating that celE is devoid of introns in its ORF region. The Orpinomyces PC-2 and *N. patriciarum* celBs are also devoid of introns [Zhou et al. (1994) *Biochem. J*. 297, 359–364; Li et al. (1997) *Appl. Environ. Microbiol*. 63, 628–635]. The lack of introns in the endoglucanase genes of the anaerobic fungi is in contrast with at least some hydrolase genes of aerobic fungi, which have introns [Li., X.-L. and Ljungdahl, L.G. (1994) *Appl. Environ. Microbiol*. 60, 3160–3166; Knowles et al. (1 987) *Trends Biotechnol*. 5, 255–261].

Table 3 provides the nucleotide and deduced amino acid sequences of celE (Cellulase CelE) from Orpinomyces sp. strain PC-2. The repeated peptides of the NCRPD and linker regions are underlined and double-underlined. The asterisk indicates the stop codon. See also SEQ ID NO:1, SEQ ID NO:2. The nucleotide sequence of celE of Orpinomyces PC-2 has been assigned Genbank accession number U97153.

The sequence of CelE of Orpinomyces PC-2, when compared with other protein sequences in the GP data bank, shared some homology with several endoglucanases of anaerobic bacteria and with CelBs of Orpinomyces and Neocallimastix. No homology with sequences of aerobic organisms was found. The highest identity was with CelBs of Orpinomyces PC-2 (72.3%) [Li et al. (1997) *Appl. Environ. Microbiol*. 63, 628–635] and *N. patriciarum* (67.9%) [Zhou et al. (1994) *Biochem. J*. 297, 359–364]. The CelBs have been assigned to glycosyl hydrolase Family 5 (formerly family A) [Henrissat, B. and Bairoch, A. (1993) *Biochem, J*. 293, 781–788], which contains endoglucanases from anaerobic bacteria, including the rumen bacteria. A comparison between the Orpinomyces PC-2 CelE and CelB amino acid sequences (SEQ ID NO: 2 and SEQ ID NO:5, respectively) is given in FIG. 1. The Orpinomyces PC-2 celE gene sequence is 99.2% identical to that of celB29 of *Orpinomyces joyonii* (submitted to the GenBank on Jul. 20, 1997, Accession Number AF01 5248). The deduced amino acid sequences differ in 6 amino acid residues.

CelE, like CelBs of Orpinomyces PC-2 and *N. patriciarum*, has the noncatalytic repeated peptide domain (NCRPD) and a linker sequence separating the catalytic domain from the NCRPD. Many hydrolytic enzymes of anaerobic fungi have a NCRPD [Gilbert et al. (1992) *Mol. Microbiol*. 6, 2065–2072; Dalrymple et al. (1997) *Microbiology* 143, 2605–2614; Durand et al. (1996) *Curr. Genet*. 30, 531–540; Fanutti et al. (1995) *J. Biol. Chem*. 270, 29314–29322; Li et al.(1997) *Appl. Environ. Microbiol*. 63, 628–635; Li et al. (1997) supra]. The NCRPD of different enzymes contain 2 or 3 repeats, which have high homology to each other and contain from 32 to 40 amino acid residues each. NCRPDs are not involved in catalysis or cellulose binding [Gilbert et al. (1992) *Mol. Microbiol*. 6, 2065–2072; Black et al. (1994) *Biochem. J*. 299, 381–387; Li et al. (1997) supra]. It has been suggested that they function as docking domains in a fashion similar to the dockerin domains of catalytic subunits of the cellulosome of *Clostridium thermocellum* [Fanutti et al. (1995) *J. Biol. Chem*. 270, 29314–29322; Choi, S.-K. and Ljungdahl, L. G. (1996) *Biochemistry* 35, 4906–4910]. Enzymes from anaerobic fungi with the NCRPDs associate as large multienzyme cellulosomal like complexes [Fanutti et al. (1995) *J. Biol. Chem*. 270, 29314–29322; Li et al. (1997) p. 424. Abstr. 97th Gen. Meet. Am. Soc. Microbiol., American Society for Microbiology, Washington, D.C.]. The presence of a NCRPD in CelE indicates that it is one of the catalytic components of Orpinomyces PC-2 cellulase/hemicellulase multienzyme complex.

Carboxymethyl cellulase (CMCase) activities were detected in cell-free extracts of *E. coli* harboring the plasmids pCEL3 (celE) or pOC1 (celB) [Li et al.(1997) *Appl. Environ. Microbiol*. 63, 628–635]. Zymogram analysis showed that the apparent molecular masses of both CelE and CelB produced in *E. coli* were approximately 42 kDa (FIG. 2), which is consistent with the deduced molecular masses of the mature CelE and CelB lacking the signal peptides and NCRPDs. The linker region between the catalytic domain and NCRPD is unstable and undergoes cleavage [Gilbert et al. (1992) *Mol. Microbiol*. 6, 2065–2072; Li et al.(1997) *Appl. Environ. Microbiol*. 63, 628–635].

The activities of cell-free extracts of *E. coli* expressing Orpinomyces CelE and CelB on various substrates were determined (Table 1). Both enzymes present in the extracts hydrolyze CMC, barley β-glucan, and lichenin. The cell-free extract containing CelE and CelB have specific activities of 3.2 and 2.9 U/mg protein with CMC as substrate. Cellobiose, cellotriose and glucose are the main products generated during prolonged hydrolysis of CMC (Table 2). No detectable hydrolysis is observed with Avicel, pNP-β-D-glucoside, oat spelt xylan or pNP-β-D-xyloside. CelE showed some activity towards pNP-β-D-cellobioside. This is in contrast to CelB, which lacks activity against this substrate. CelB from *N. patriciarum* also has only a low level of activity against pNP-β-D-cellobioside [Xue et al. (1992) *J. Gen. Microbiol*. 138, 1413–1420].

Hydrolysis products formed during the action of the recombinant CelE and CelB on cello-oligosaccharides were determined by HPLC (Table 2). Neither of the two enzymes hydrolyze cellobiose. CelE slowly hydrolyzes cellotriose to cellobiose and glucose, but CelB is unable to hydrolyze this substrate. This is consistent with the fact that CelE hydrolyzed pNP-β-D-cellobioside (Table 1). Cellotetraose was degraded into cellobiose, cellotriose and glucose, whereas cellopentaose was largely converted into cellobiose and cellotriose and some glucose. In the case of CelB towards cellopentaose, some cellotetraose was present in the products and it was further converted into cellobiose, cellotriose, and glucose. These observations, together with the product profiles of the hydrolysis of CMC and the substrate specificity determinations (Table 1) indicate that CelE and CelB are endoglucanases.

The genes of celE and celB [Li et al.(1997) *Appl. Environ. Microbiol*. 63, 628–635] of Orpinomyces PC-2 and of celB [Zhou et al. (1994) *Biochem. J*. 297, 359–364] of *N. patriciarum* are devoid of introns. They are highly homologous to each other (FIG. 1) and genes encoding rumen bacterial endoglucanases. This seems to indicate that the Orpinomyces PC-2 celE and celB probably were originally transferred from rumen bacteria and subsequently duplicated in the fungus. It seems that gene duplication is a common phenomenon in anaerobic fungi. It has been postulated for multiple mannanases [Millward-Sadler et al. (1996) *FEMS Microbiol. Letts*. 141, 183–188] and cellobiohydrolases [Li et al. (1997) *Appl. Environ. Microbiol*. 63, 4721–4728].

It will be understood by those skilled in the art that other nucleic acid sequences besides that disclosed herein for CelE will function as coding sequences synonymous with the exemplified coding sequences. Nucleic acid sequences are synonymous if the amino acid sequences encoded by those nucleic acid sequences are the same. The degeneracy of the genetic code is well known to the art. For many amino acids, there is more than one nucleotide triplet which serves as the codon for a particular amino acid, and one of ordinary skill in the art understands nucleotide or codon substitutions which do not affect the amino acid(s) encoded. It is further understood in the art that codon substitutions to conform to common codon usage in a particular recombinant host cell is sometimes desirable.

Specifically included in this invention are sequences from other strains of Orpinomyces and from other anaerobic fungi which hybridize to the sequence disclosed for celE under stringent conditions. Stringent conditions refer to conditions understood in the art for a given probe length and nucleotide composition and capable of hybridizing under stringent conditions means annealing to a subject nucleotide sequence, or its complementary strand, under standard conditions (i.e., high temperature and/or low salt content) which tend to disfavor annealing of unrelated sequences, (indicating about 95–100% nucleotide sequence identity). Also specifically included in this invention are sequences from other strains of Orpinomyces species and other anaerobic fungi which hybridize to the sequences disclosed for celE under moderately stringent conditions. Moderately stringent conditions refer to conditions understood in the art for a given probe sequence and "conditions of medium stringency" means hybridization and wash conditions of 50°–65° C., 1×SSC and 0.1% SDS (indicating about 80–95% similarity). Also specifically included in this invention are sequences from other strains of Orpinomyces from other anaerobic fungi, and from other organisms, including humans, which hybridize to the sequences disclosed for celE under highly stringent conditions. Highly stringent conditions refer to conditions understood in the art for a given probe sequence and "conditions of high stringency" means hybridization and wash conditions of 65–68° C, 0.1×SSC and 0.1% SDS (indicating about 95–100% similarity). Hybridization assays and conditions are further described in Sambrook et al. (1989).

A method for identifying other nucleic acids encoding celE-homologous enzymes is also provided wherein nucleic acid molecules encoding cellulases are isolated from an anaerobic fungus, and nucleic acid hybridization is performed with the nucleic acid molecules and a labeled probe having a nucleotide sequence that includes all or part of nucleotide sequence SEQ ID NO:1. By this method, silencing genes similar to the exemplified celE gene may be identified and isolated from other strains of Orpinomyces or other anaerobic fungi. All or part of a nucleotide sequence refers specifically to all continuous nucleotides of a nucleotide sequence, or e.g. 1000 continuous nucleotides, 500 continuous nucleotides, 100 continuous nucleotides, 25 continuous nucleotides, and 15 continuous nucleotides.

Sequences included in this invention are those amino acid sequences which are 75% similar to the amino acid sequences encoded by the exemplified Orpinomyces strain PC-2 celE. Sequences included in this invention are also those amino acid sequences which are 80, 85, 90, 95 to 100%, and all integers between 75% and 100%, similar to the amino acid sequences encoded by exemplified Orpinomyces celE.

It is well-known in the biological arts that certain amino acid substitutions may be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate, and isoleucine and valine, are both pairs of similar amino acids. Similarity between amino acid pairs has been assessed in the art in a number of ways. For example, Dayhoff et al. (1978) in *Atlas of Protein Sequence and Structure*, Volume 5, Supplement 3, Chapter 22, pp. 345–352, which is incorporated by reference herein provides frequency tables for amino acid substitutions which can be employed as a measure of amino acid similarity. Dayhoff et al.'s frequency tables are based on comparisons of amino acid sequences for proteins having the same function from a variety of evolutionarily different sources.

Monoclonal or polyclonal antibodies, preferably monoclonal, specifically reacting with the particular cellulase (CelE) of the present invention may be made by methods known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Harnes and Higgins (eds.) (1985) *Nucleic Acid Hybridization*, IRL Press, Oxford, UK; and Setlow and Hollaender (1979) *Genetic Engineering: Principles and Methods*, Vols. 1–4, Plenum Press, New York. Abbreviations and nomenclature, where employed, are deemed standard in the field and commonly used in professional journals such as those cited herein.

Each reference cited in the present application is incorporated by reference herein.

The following examples are provided for illustrative purposes, and is not intended to limit the scope of the invention as claimed herein. Any variations in the exemplified articles which occur to the skilled artisan are intended to fall within the scope of the present invention.

EXAMPLES

Example 1

Strains, Vectors and Orpinomyces cDNA Library

Orpinomyces sp. strain PC-2 [Borneman et al. (1989) *Appl. Environ. Microbiol.* 55, 1066–1073] was grown as previously described [Chen et al. (1997) *J. Bacteriol.* 179, 6028–6034]. *Escherichia coli* XL 1-Blue, λZAPII, and pBluescript SK(−) were from Stratagene Cloning Systems (La J.olla, Calif.).

Construction of a CDNA library for Orpinomyces PC-2 in λZAPII (Stratagene)[Chen et al. (1995) *Proc. Natl. Acad. Sci. USA* 92, 2587–2591] and the isolation of cellulase producing plaques were carried out as described previously [Chen et al. (1997) *J. Bacteriol.* 179, 6028–6034], except that carboxymethylcellulose (CMC) was used instead of lichenin as the substrate. Top agar containing 5 mM isopropyl-β-D-thiogalactoside to induce recombinant gene expression via lac promoter sequences and 0.2% remazol brilliant blue (RRB)-carboxymethyl cellulose (CMC) (InterSpex Products, Inc., Foster city, Calif.) or RBB-xylan (Sigma Chemical Co., St. Louis, Mo.) was used to identify cellulose- and xylanase-producing clones. Positive clones were identified by their clear haloes on a blue background due to diffusion of RBB after hydrolysis of RBB-CMC or RBB-xylan. Pure clones were obtained after a secondary screening. The isolation of pBluescript subclones, sequencing of inserted DNA and data analysis were done as described in Chen et al. (1997) *J. Bacteriol.* 179, 6028–6034.

Example 2

Analysis of Genomic DNA

Oligonucleotides 5'ATGAAGTTTTTCAAAAACACTT-TAGC3' (SEQ ID NO:3) and 5'TTATTTATGGTGGT-CAATGGT3' (SEQ ID NO:4), corresponding to opposite strands of the end regions of celE open reading frame (ORF), were used as primers with genomic DNA [Chen et al. (1997) *J. Bacteriol.* 179, 6028–6034] and the cDNA library as templates for polymerase chain reactions (PCR) which were performed on a 480 Thermal Cycler (Perkin-Elmer, Norwalk, Conn.). Amplification was for 30 cycles with each cycle consisting of 90 s of melting at 95° C., 60 s of annealing at 42° C., and 60 s of extension at 72° C.

Example 3

Zymogram Analysis, Enzyme Assays, and Analytical Methods

Sodium dodecyl sulfate-polyacrylamide gel electrophoresis (SDS-PAGE) [Laemmli, U. K. (1970) *Nature* 227, 680–685], zymogram analysis after SDS-PAGE [Beguin, P. (1983) *Anal. Biochem.* 131, 333–336], and determinations of cellulolytic activities using CMC, other polysaccharides, and p-nitrophenol (pNP) glycosides as substrates were done as previously described [Chen et al. (1997) *J. Bacteriol.* 179, 6028–6034; Li et al. (1997) supra]. Protein concentration was determined using the method of Bradford [Bradford, M. M. (1976) *Anal. Biochem.* 72, 248–254].

Sugars released from cello-oligosaccharides and CMC were analyzed with a Hewlett-Packard 1100 series HPLC equipped with an autoinjector and a 1047A RI detector using a Bio-Rad Aminex HPX-42A carbohydrate column (Bio-Rad Laboratories, Hercules, Calif.). Water was used as the mobile phase at a flow rate of 0.6 ml/min.

TABLE 1

Substrate specificity of CelE and CelB produced in *E. coli*[a]

| | Specific activity (U/mg protein) | |
|---|---|---|
| Substrate[b] | CelE | CelB |
| CMC | 3.2 | 2.9 |
| Barley β-glucan | 14.5 | 9.7 |
| Lichenin | 9.2 | 9.0 |
| pNP-β-D-cellobioside | 0.2 | ND[c] |

[a]Assays were performed at 40° C. and pH 6.0 (50 mM sodium citrate) for 10 min (pNP-β- glycosides), 15 min (oat spelt xylan, barley β-glucan and lichenin), 30 min (CMC), and 4 h (Avicel), respectively. Enzyme unit (U) was defined as the amount of enzyme required to release 1 μmol of glucose equivalent per min.
[b]The activity towards Avicel, pNP-β-D-glucoside, oat spelt xylan, or pNP-β-D-xyloside was less than 1.0% of that of CMC.
[c]ND means not detectable (activity less that 1.0% of that on CMC).

TABLE 2

HPLC analysis of products of cello-oligosaccharide and CMC hydrolysis by CelE and CelB produced in *E. coli*[a]

| | | Products or residual substrates (μmol/ml) | | | |
|---|---|---|---|---|---|
| Enzyme | Substrate | G1 | G2 | G3 | G4 |
| CelE | Cellotriose (G3, 4 h) | 0.1 | 0.1 | 2.8 | — |
| | Cellotriose (G3, 20 h) | 0.7 | 0.8 | 2.0 | — |
| | Cellotetraose (G4, 4 h) | 1.0 | 4.1 | 0.8 | — |
| | Cellopentaose (G5, 4 h) | 0.3 | 3.2 | 2.6 | — |
| | CMC (4 h) | 0.1 | 0.5 | 0.2 | — |
| CelB | Cellotriose (G3, 4 h) | — | — | 3.0 | — |
| | Cellotriose (G3, 20 h) | — | — | 2.8 | — |
| | Cellotetraose(G4, 4 h) | 0.9 | 3.0 | 1.0 | 0.4 |
| | Cellopentaose (G5, 4 h) | 0.4 | 2.5 | 1.8 | 0.7 |
| | CMC (4 h) | 0.1 | 0.4 | 0.2 | — |

[a]Reaction mixtures contained 0.2–0.3 U/ml enzyme (CMC as substrate) and 3 mM of cello-oligosaccharides or 0.7% (w/v) CMC in 20 mM sodium citrate. Reactions were at pH 6.0 and 40° C. and for times as indicated.

TABLE 3

Nucleotide and Deduced Amino Acid Sequence for Orpinomyces Strain PC-2 Cel E

```
AAAATAATAAATAACTTATTTATTAAATATCAGTAAAAATGAAGTTTTTCAAAAACACTTTAGCTTTACTCACCTTAGTCATTGCTGGTTCAAATGCTAT
                                     M  K  F  F  K  N  T  L  A  L  L  T  L  V  I  A  G  S  N  A  M      21

GAGAAATATTCCATCCAAAGATTTAGTTAAGGAATTAAACATTGGTTGGAATTTAGGTAATGCTTTAGATGCTCATTGTTTAGATAAATTAGATTATAAT
 R  N  I  P  S  K  D  L  V  K  E  L  N  I  G  W  N  L  G  N  A  L  D  A  H  C  L  D  K  L  D  Y  N    54

AAAGATCAACTTGCTTCTGAAACTTGTTGGGCTAATCCAAAGGCTACTCCAGGACTTTTCAGTGCATTAAAGAATCAAGGTTTTAATGTTTTCCGTATTC
 K  D  Q  L  A  S  E  T  C  W  A  N  P  K  A  T  P  G  L  F  S  A  L  K  N  Q  G  F  N  V  F  R  I  P  88

CAACCACTTGGACCGGTCACTTTGGTAATGGTCCAGATTACAAAATTAGTGATGTTTGGATGAGAAGAGTTCATGAAGTTGTTGATTATGCTCTTAACAC
    T  T  W  T  G  H  F  G  N  G  P  D  Y  K  I  S  D  V  W  M  R  R  V  H  E  V  V  D  Y  A  L  N  T 121

TGGAAGCTACGTCATCTTAAATATTCACCATGAAAATTGGAATTATGCTTTCTCTAACAATTTACAAAAGGCAAAACCAATTTTAGCTGCTATCTGGAAA
    G  S  Y  V  I  L  N  I  H  H  E  N  W  N  Y  A  F  S  N  N  L  Q  K  A  K  P  I  L  A  A  I  W  K 154
```

TABLE 3-continued

Nucleotide and Deduced Amino Acid Sequence for *Orpinomyces* Strain PC-2 Cel E

```
CAAATTGCTGCTGAATTCGCTAACTATGATGAACATTTAATTTTCGAAGGTATGAATGAACCAAGAAAGGTTGATCATCCAAATGAATGGAATGGTGGTG
 Q  I  A  A  E  F  A  N  Y  D  E  H  L  I  F  E  G  M  N  E  P  R  K  V  D  H  P  N  E  W  N  G  G  D    188

ACCAAGAAGGTTGGGACTTCGTTAATGAAATGAATGCTGTCTTCCTTCAAACTGTTCGTGCCTCTGGTGGTAACAATGCTATTCGTCACCTTATGATTCC
  Q  E  G  W  D  F  V  N  E  M  N  A  V  F  L  Q  T  V  R  A  S  G  G  N  N  A  I  R  H  L  M  I  P    221

AACTTATGCTGCTTGTGTTAACGATGGTGCTCTTGAATCTTACGTTAGAAAATTCCCAACTAATGATAATAAGGTTATTGCTTCTGTCCACTCTTATGTT
  T  Y  A  A  C  V  N  D  G  A  L  E  S  Y  V  R  K  F  P  T  N  D  N  K  V  I  A  S  V  H  S  Y  V    254

CCATATAACTTTGCCTTAAATACTGGCGCCGGTGCTGAAAAGACTTTCGGTTCCACTAGCGATATTGAATGGGCTATGAACAACATCAAGAGATTCTTAG
  P  Y  N  F  A  L  N  T  G  A  G  A  E  K  T  F  G  S  T  S  D  I  E  W  A  M  N  N  I  K  R  F  L    288

TTGACAGAAATATTCCAGTTATAATTGGTGAATTCGGAGCTATGAACCGTGACAATGAATCTGAACGTGCTAGATGGGCTGAATACTACATTAAGAGTGC
   D  R  N  I  P  V  I  I  G  E  F  G  A  M  N  R  D  N  E  S  E  R  A  R  W  A  E  Y  Y  I  K  S  A   321

CACTGCTATGGGTGTTCCATGTGTCTTATGGGATAATGGTTACACTCAAGGTACTGGTGAACTTTTCGGTGTTATTGACCGTAACTCTTACAGAATCATT
  T  A  M  G  V  P  C  V  L  W  D  N  G  Y  T  Q  G  T  G  E  L  F  G  V  I  D  R  N  S  Y  R  I  I    354

TTCCAACAATTCATTAATGGCTTAATGAAGGGATTAGGTGGTAAGAAGACCGTTGCTCCAGCTCCAACTACTACTATTACTACTACTACTGTTAAAG
  F  Q  Q  F  I  N  G  L  M  K  G  L  G  G  K  K  T  V  A  P  A  P  T̲  T̲  T̲  I̲  T̲  T̲  T̲  T̲  T̲  V̲  K̲  V̲    388

TTCAACCAACTAATAATAATGAATGTTTCAGTACTAGACTTGGTTACAGCTGTTGTAATGGTTGTGATGTCTTTTACACTGATAATGATGGTAAATGGGG
  Q̲  P̲  T̲  N̲  N̲  N̲  E  C̲  F̲  S̲  T̲  R̲  L̲  G̲  Y̲  S̲  C̲  C̲  N̲  G̲  C̲  D̲  V̲  F̲  Y̲  T̲  D̲  N̲  D̲  G̲  K̲  W̲  G̲    421

TGTTGAAAACGGTAACTGGTGTGGTATTAAGTCATCTTGTGATAACAACCAACGTTATTGCTGGTCTGAAAGACTTGGTTACCCATGTTGTCAATATACC
  V̲  E̲  N̲  G̲  N̲  W̲  C̲  G̲  I̲  K̲  S  S  C  D  N  N  Q  R  Y  C̲  W̲  S̲  E̲  R̲  L̲  G̲  Y̲  P̲  C̲  C̲  Q̲  Y̲  T̲    454

ACCAATGTTGAATACACCGATAATGATGGTAGATGGGGTGTTGAAAATGGTAACTGGTGTGGTATTTATTAAATTACTAAATAAATTTATATAAATAGAA
  T̲  N̲  V̲  E̲  Y̲  T̲  D̲  N̲  D̲  G̲  R̲  W̲  G̲  V̲  E̲  N̲  G̲  N̲  W̲  C̲  G̲  I̲  Y̲  *                          477

ATAAATTATTTAGTAAAATAAATAAAAAAAAA
```

The repeated peptides of the NCPRD and linker regions are underlined and double-underlined. The asterisk indicates the translation termination codon.

---

We claim:

1. A non-naturally occurring recombinant DNA molecule comprising a nucleotide sequence encoding a CelE cellulase, said CelE cellulase having characteristics of an endoglucanase having hydrolytic activity for carboxymethylcellulose, barley β-glucan, lichenin and para-nitrophenyl-β-D-cellobioside and said nucleotide sequence hybridizing to a DNA molecule having a nucleotide sequence as given in SEQ ID NO:1, nucleotides under conditions of medium stringency, wherein conditions of medium stringency are hybridization and wash at a temperature from 50° C. to 65° C., 1×SSC, 0.1% sodium dodecyl sulfate.

2. The non-naturally occurring recombinant DNA molecule of claim 1 wherein said nucleotide sequence encodes a CelE cellulase having an amino acid sequence as given in SEQ ID NO:2.

3. The non-naturally occurring recombinant DNA molecule of claim 1 wherein said nucleotide sequence encoding said CelE cellulase is as given in SEQ ID NO:1, nucleotides 39–1469, exclusive of a transcription termination codon.

4. A recombinant host cell comprising the non-naturally occurring recombinant DNA molecule of claim 1.

5. The recombinant host cell of claim 4 wherein the nucleotide sequence encodes a mature CelE cellulase having an amino acid sequence as given in SEQ ID NO:2.

6. The recombinant host cell of claim 5 wherein said nucleotide sequence encoding said CelE cellulase is as given in SEQ ID NO:1, nucleotides 39 to 1462, exclusive of a translation termination codon.

7. A method of producing recombinant CelE cellulase in a recombinant host cell, said method comprising the steps of:

(a) transforming or transfecting a host cell to contain and express a non-naturally occurring recombinant DNA molecule comprising a nucleotide sequence encoding a CelE cellulase, said cellulase having characteristics of an endoglucanase having hydrolytic activity for carboxymethylcellulose, barley β-glucan, lichenin and para-nitrophenyl-β-D-cellobioside and nucleotide sequence hybridizing to a DNA molecule having a nucleotide sequence as given in SEQ ID NO:1, said nucleotides under conditions of medium stringency wherein conditions of medium stringency are hybridization and wash at a temperature from 50° C. to 65° C. 1×SSC, 0.1% sodium dodecyl sulfate; and (b) culturing the recombinant host cell of step (a) under conditions for expression of the CelE cellulase.

8. The method of claim 7 wherein said nucleotide sequence encodes a CelE cellulase having an amino acid sequence as given in SEQ ID NO:2.

9. The method of claim 8 wherein said nucleotide sequence encoding said CelE cellulase is as given in SEQ ID NO:1, nucleotides 39–1469, exclusive of a transcription termination codon.

* * * * *

UNITED STATES PATENT AND TRADEMARK OFFICE
CERTIFICATE OF CORRECTION

PATENT NO. : 6,110,720

DATED : August 29, 2000

INVENTOR(S) : Li et al.

It is certified that error appears in the above-identified patent and that said Letters Patent is hereby corrected as shown below:

In the Abstract:

In the first line of the abstract, delete "CDNA" and replace with --cDNA--.

At column 1, line 63, delete "CeiC" and replace with --CelC--.

At column 5, line 18, delete "GP" and replace with --GCG--.

At column 5, line 35, delete the space in "AFO1 5248" to read --AF015248--.

At column 8, line 53, delete "La J.olla," and replace with --La Jolla,--.

At column 8, line 63, delete "(RRB)" and replace with --(RBB)--.

UNITED STATES PATENT AND TRADEMARK OFFICE
CERTIFICATE OF CORRECTION

PATENT NO.  : 6,110,720

DATED       : August 29, 2000

INVENTOR(S) : Li et al.

It is certified that error appears in the above-identified patent and that said Letters Patent is hereby corrected as shown below:

In the title line of Table 3, columns 9 and 10, delete the space in "Cel E" to read --CelE--.

In the title line of Table 3, columns 11 and 12, delete the space in "Cel E" to read --CelE--.

In Table 3, columns 11 and 12, delete the amino acid "O" at position 389, and replace with --Q--.

In Table 3, columns 11 and 12, delete the amino acid "O" at position 452 and replace with --Q--.

In the legend for Table 3, columns 11 and 12, delete "NCPRD" and replace with --NCRPD--.

In the claims:

In column 21, line 33, delete "transcription" and replace with --translation--.

In column 21, line 41, delete "1462" and replace with --1469--.

In column 22, line 39, delete "transcription" and replace with --translation--.

Signed and Sealed this

Fifteenth Day of May, 2001

Attest:

NICHOLAS P. GODICI

Attesting Officer    Acting Director of the United States Patent and Trademark Office

UNITED STATES PATENT AND TRADEMARK OFFICE
CERTIFICATE OF CORRECTION

PATENT NO.   : 6,110,720
DATED        : August 29, 2000
INVENTOR(S)  : Li et al.

It is certified that error appears in the above-identified patent and that said Letters Patent is hereby corrected as shown below:

Title page,
Item [57], ABSTRACT,
Line 1, delete "CDNA" and replace with -- cDNA --.

Column 1,
Line 63, delete "CeiC" and replace with -- CelC --.

Column 5,
Line 18, delete "GP" and replace with -- GCG --.
Line 35, delete the space in "AFO1 5248" to read -- AFO15248 --.

Column 8,
Line 53, delete "La J.olla," and replace with -- La Jolla, --.
Line 63, delete "(RRB)" and replace with -- (RBB) --.

Columns 9 and 10,
Table 3, delete the space in "Cel E" to read -- CelE --.

Columns 11 and 12,
Table 3, delete the space in "Cel E" to read -- CelE --.
Table 3, delete the amino acid "O" at position 389, and replace with -- Q --.
Table 3, delete the amino acid "O" at position 452 and replace with -- Q --.
Table 3, delete "NCPRD" and replace with -- NCRPD --.

Column 21,
Line 33, delete "transcription" and replace with -- translation --.
Line 41, delete "1462" and replace with -- 1469 --.

UNITED STATES PATENT AND TRADEMARK OFFICE
CERTIFICATE OF CORRECTION

PATENT NO. : 6,110,720
DATED : August 29, 2000
INVENTOR(S) : Li et al.

It is certified that error appears in the above-identified patent and that said Letters Patent is hereby corrected as shown below:

Column 22,
Line 39, delete "transcription" and replace with -- translation --.

Signed and Sealed this

Twenty-first Day of September, 2004

JON W. DUDAS
*Director of the United States Patent and Trademark Office*